(12) United States Patent
Yamamoto et al.

(10) Patent No.: US 9,326,688 B2
(45) Date of Patent: May 3, 2016

(54) OBJECT INFORMATION ACQUIRING APPARATUS

(71) Applicant: CANON KABUSHIKI KAISHA, Tokyo (JP)

(72) Inventors: Hiroshi Yamamoto, Kawasaki (JP); Yukio Furukawa, Sagamihara (JP); Hiroshi Nishihara, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 401 days.

(21) Appl. No.: 13/776,888

(22) Filed: Feb. 26, 2013

(65) Prior Publication Data

US 2013/0231549 A1  Sep. 5, 2013

(30) Foreign Application Priority Data

Mar. 2, 2012  (JP) ................. 2012-047005

(51) Int. Cl.
*A61B 8/00* (2006.01)
*A61B 6/00* (2006.01)
*A61B 5/00* (2006.01)

(52) U.S. Cl.
CPC .............. *A61B 5/0095* (2013.01); *A61B 5/708* (2013.01)

(58) Field of Classification Search
None
See application file for complete search history.

(56) References Cited

U.S. PATENT DOCUMENTS

| | | | | |
|---|---|---|---|---|
| 4,502,755 A * | 3/1985 | Mori | .................... | G03B 21/625 359/456 |
| 6,212,421 B1 * | 4/2001 | Vo-Dinh et al. | ............... | 600/407 |
| 6,542,245 B2 | 4/2003 | Toida | ............... | 356/480 |
| 8,144,327 B2 | 3/2012 | Nakajima et al. | ............. | 356/432 |
| 8,480,584 B2 | 7/2013 | Kanayama et al. | ........... | 600/407 |
| 2009/0005685 A1 * | 1/2009 | Nagae et al. | .................. | 600/459 |
| 2009/0189256 A1 * | 7/2009 | Yoshimura | .......... | H01L 21/6835 257/621 |
| 2010/0030078 A1 * | 2/2010 | Mikami | ........................ | 600/443 |
| 2010/0053618 A1 * | 3/2010 | Nakajima et al. | ............. | 356/432 |
| 2011/0230762 A1 * | 9/2011 | Tokita et al. | .................. | 600/437 |
| 2011/0245667 A1 * | 10/2011 | Tokita | ................. | A61B 5/0048 600/437 |
| 2011/0251475 A1 * | 10/2011 | Tokita et al. | .................. | 600/407 |
| 2011/0270071 A1 | 11/2011 | Furukawa | ...................... | 600/407 |
| 2011/0303015 A1 * | 12/2011 | Ichihara et al. | ................. | 73/656 |
| 2012/0257472 A1 * | 10/2012 | Yoda | .................... | A61B 5/0059 367/7 |

(Continued)

FOREIGN PATENT DOCUMENTS

| | | |
|---|---|---|
| CN | 1321887 | 11/2001 |
| CN | 1650794 | 8/2005 |

(Continued)

OTHER PUBLICATIONS

M. Xu et al., "Photoacoustic Imaging in Biomedicine", *Review of Scientific Instruments*, vol. 77, pp. 041101-1-041101-22 (2006).

(Continued)

*Primary Examiner* — Long V Le
*Assistant Examiner* — Bradley Impink
(74) *Attorney, Agent, or Firm* — Fitzpatrick, Cella, Harper & Scinto

(57) ABSTRACT

The present invention employs an object information acquiring apparatus that includes a light source, a holding plate configured to hold an object, a supporting unit configured to support the holding plate, and a probe configured to receive, via the holding plate, an acoustic wave generated from the object on which light is irradiated from the light source. A light reflecting member is provided between the supporting unit and the holding plate.

13 Claims, 8 Drawing Sheets

(56) References Cited

U.S. PATENT DOCUMENTS

| | | | |
|---|---|---|---|
| 2013/0061678 A1 | 3/2013 | Yamamoto et al. | 73/602 |
| 2013/0112001 A1 | 5/2013 | Furukawa | 73/655 |
| 2013/0165765 A1 | 6/2013 | Nishihara | 600/407 |

FOREIGN PATENT DOCUMENTS

| | | |
|---|---|---|
| JP | 2006-208050 | 8/2006 |
| JP | 2010-75681 | 4/2010 |
| WO | WO 2011132412 A1 * | 10/2011 |

OTHER PUBLICATIONS

S.E. Vaartjes et al., "First Clinical Trials of the Twente Photoacoustic Mammoscope (PAM)", *SPIE-OSA*, vol. 6629, pp. 662917-1-662917-12.

Office Action issued on Jul. 22, 2014, in Chinese (P.R. China) counterpart application 201310058955.8, with translation.

Extended European Search Report dated Jun. 11, 2013, issued in counterpart European Patent Application No. 13001022.6.

* cited by examiner

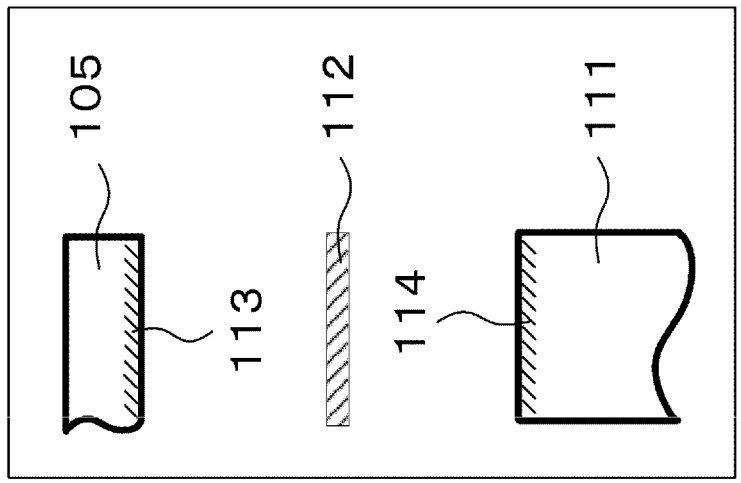
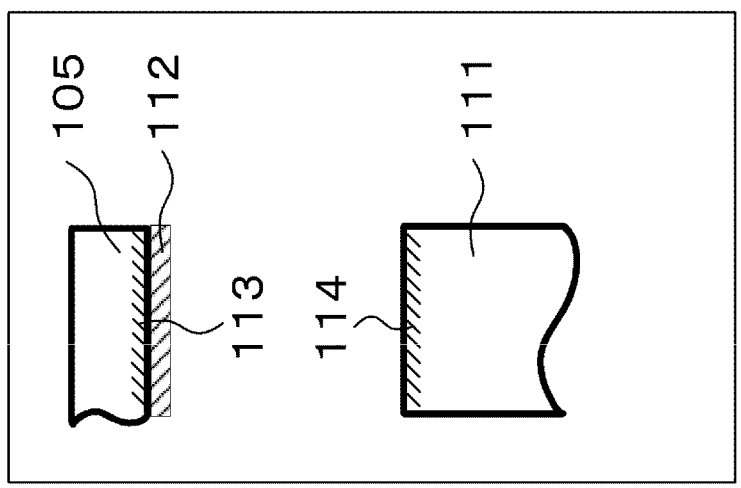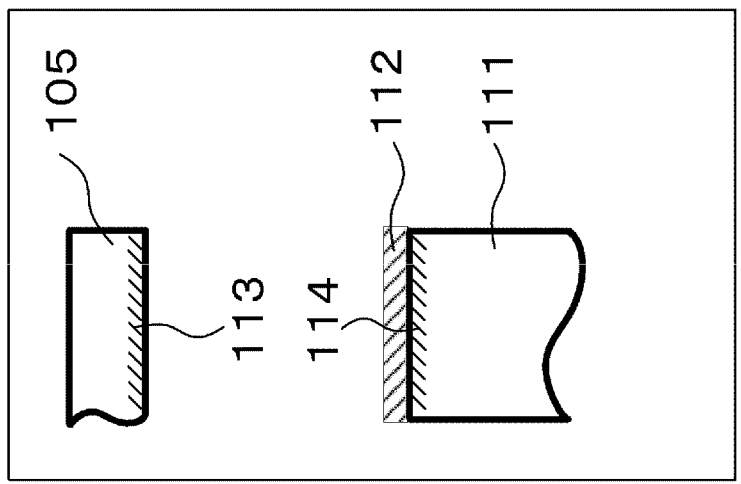

OBJECT INFORMATION ACQUIRING APPARATUS

BACKGROUND OF THE INVENTION

1. Field of the Invention

The present invention relates to an object information acquiring apparatus.

2. Description of the Related Art

As one of methods of calculating an optical property value such as an absorption coefficient in a living organism, there is photoacoustic tomography (hereinafter, PAT) that makes use of a characteristic of an ultrasound wave that scatters less in the living organism than light (Non Patent Literature 1: M. Xu, L. Wang "Photoacoustic imaging in biomedicine", Review of scientific instruments, 77, 041101(2006)). When pulsed light generated from a light source is irradiated on the living organism, the light propagates while diffusing in the living organism. A light absorber included in the living organism absorbs the propagated light and generates an acoustic wave (typically, an ultrasound wave). By receiving the acoustic wave with a probe and analyzing the received signal, it is possible to obtain an initial sound pressure distribution caused by the absorber in the living organism. An absorption coefficient distribution can be obtained by taking into account a distribution of the light with respect to the initial sound pressure distribution.

The sound pressure of the acoustic wave in the PAT is proportional to an amount of local light that reaches the light absorber. The light irradiated on the living organism suddenly attenuates in the living organism because of the scattering and the absorption. Therefore, the sound pressure of the acoustic wave generated in a deep tissue in the living organism substantially attenuates according to the distance from the light irradiated region. Therefore, in order to obtain information concerning a living organism deep part, it is necessary to reduce the thickness of an object region. As an example, in Susanne E. et al. "First clinical trials of the Twente Photoacoustic Mammoscope (PAM)" (Non Patent Literature 2), an object is held and pressured by two holding plates to reduce the thickness of the object. When the holding plates are used, in order to suppress deformation due to the pressuring, in general, a supporting unit with high rigidity made of metal, ceramic, or the like is provided around the holding plates.

In a photoacoustic signal acquiring apparatus, when direct light from a light source or light propagated in the living organism is irradiated on a probe surface, an acoustic wave is generated on the probe surface and the acoustic wave causes a noise. The acoustic wave generated on the probe surface is received by the probe first. An acoustic wave from the living organism is received by the probe before a response to a signal of the received acoustic wave ends. In other words, the signal received by the probe is a signal on which noise is superimposed. In the photoacoustic signal acquiring apparatus, when information concerning the inside of an object is converted into an image on the basis of the signal received by the probe, noise caused by an acoustic wave generated in the supporting unit is an artifact. As a result, accuracy in using the image for medical diagnosis is deteriorated.

Therefore, Japanese Patent Application Laid-Open No. 2010-75681 (Patent Literature 1) discloses an example in which a light reflecting member is provided on a probe surface, whereby an acoustic wave generated on the probe surface by diffused light emitted to the outside of a living organism is reduced to reduce noise.

Patent Literature 1: Japanese Patent Application Laid-Open No. 2010-75681

Non Patent Literature 1: M. Xu, L. Wang "Photoacoustic imaging in biomedicine", Review of scientific instruments, 77, 041101(2006)

Non Patent Literature 2: Susanne E. et al. "First clinical trials of the Twente Photoacoustic Mammoscope (PAM)"

SUMMARY OF THE INVENTION

However, in view of the apparatus described in M. Xu, L. Wang "Photoacoustic imaging in biomedicine", Review of scientific instruments, 77, 041101(2006), when the supporting unit that supports the holding plates is made of a material having high rigidity such as metal, an acoustic wave generated from the supporting unit by light scattering from the inside of the organism causes noise. In particular, in view of a reduction in the size of the apparatus, since the supporting unit is provided closer to the probe, the probe tends to be affected by the noise. Even if Japanese Patent Application Laid-Open No. 2010-75681 is applied to solve the problem, the problem cannot be solved because a mechanism for reducing the acoustic wave generated in the supporting unit is not provided.

The present invention has been devised in view of the problem and it is an object of the present invention to reduce, in the PAT, the noise due to the acoustic wave generated in the supporting unit that supports the holding plates.

The present invention provides an object information acquiring apparatus comprising:

a light source;

a holding plate configured to hold an object;

a supporting unit configured to support the holding plate; and a probe configured to receive, via the holding plate, an acoustic wave generated from the object on which light is irradiated from the light source, wherein a light reflecting member is provided between the supporting unit and the holding plate.

According to the apparatus, it is possible to reduce, in the PAT, the noise due to the acoustic wave generated in the supporting unit that supports the holding plates.

Further features of the present invention will become apparent from the following description of exemplary embodiments with reference to the attached drawings.

BRIEF DESCRIPTION OF THE DRAWINGS

FIGS. 2A to 2C are diagrams for explaining positions where a light reflecting member is provided;

DESCRIPTION OF THE EMBODIMENTS

Figure 1:
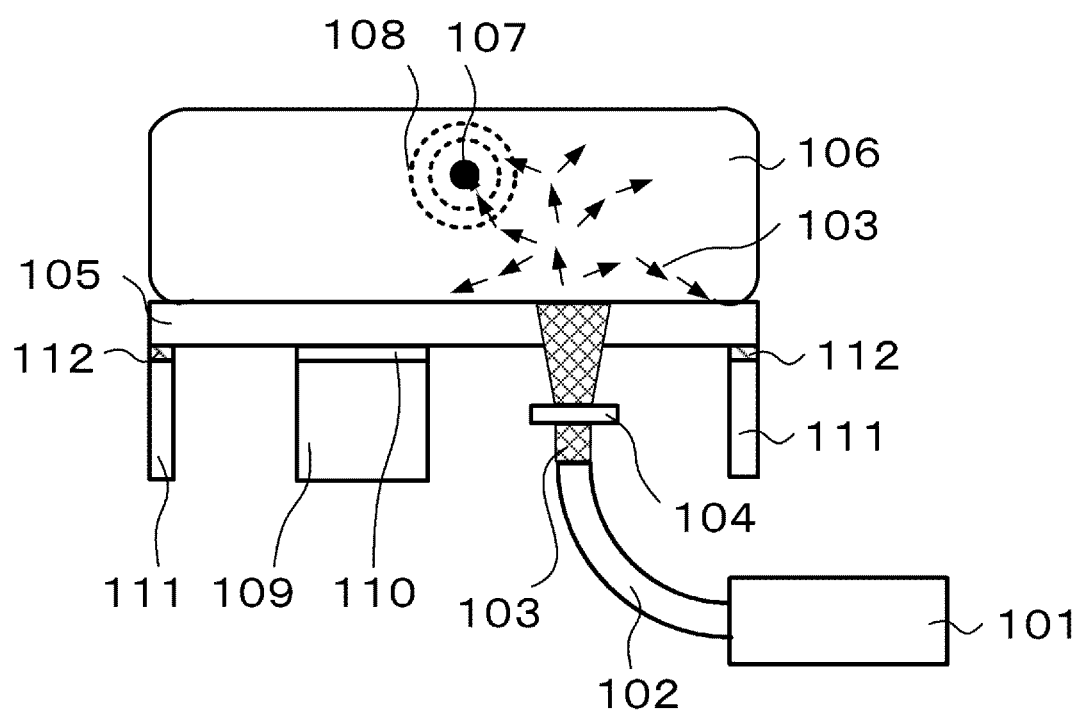
FIG. 1 is a schematic configuration diagram showing functional blocks of an apparatus according to a first embodiment.

Preferred embodiments of the present invention are explained below with reference to the drawings. However, dimensions, materials, and shapes of components explained below, relative arrangement of the components, and the like should be changed as appropriate according to the configuration of an apparatus to which the present invention is applied and various conditions and are not meant to limit the scope of the present invention to the below description.

An object information acquiring apparatus according to the present invention is an apparatus that makes use of a photoacoustic effect for irradiating light (an electromagnetic wave) on an object to thereby receive an acoustic wave generated in the object and acquiring object information as image data. The object information is property information indicating a generation source distribution of the acoustic wave, an initial sound pressure distribution in the object, an optical energy absorption density distribution and an absorption coefficient distribution derived from the initial sound pressure distribution, or a concentration distribution of a substance included in a tissue. The concentration distribution of the substance is, for example, an oxygen saturation distribution or an oxygenated/reduced hemoglobin concentration distribution.

The acoustic wave in the present invention is typically an ultrasound wave and includes elastic waves called a sound wave, an ultrasound wave, and an acoustic wave. The acoustic wave caused by the photoacoustic effect is referred to as photoacoustic wave or light-induced ultrasound wave. An acoustic detector (e.g., a probe) receives an acoustic wave generated in an object.

The photoacoustic wave, an electric signal converted from the photoacoustic wave by the probe, or a signal obtained by applying desired signal processing such as amplification or digital conversion to the electric signal is sometimes referred to as photoacoustic signal. Therefore, the object information acquiring apparatus according to the present invention can also be grasped as a photoacoustic signal acquiring apparatus. When an acquired photoacoustic signal is converted into an image for the purpose of medical diagnosis or the like, the object information acquiring apparatus can also be grasped as a photoacoustic imaging apparatus. In the following explanation, the photoacoustic signal acquiring apparatus and the photoacoustic imaging apparatus are described as examples of the object information acquiring apparatus.

(Photoacoustic Signal Acquiring Apparatus)

A photoacoustic signal acquiring apparatus according to an embodiment is an apparatus that acquires information concerning the inside of an object. The photoacoustic signal acquiring apparatus according to this embodiment includes, as basic hardware components, a light source, a probe that receives an acoustic wave, a holding plate that holds an object, and a supporting unit that supports the holding plate. Pulsed light emitted from the light source is irradiated on the object through the holding plate. Optical members such as lens, a mirror, a diffuser, and an optical fiber may be interposed between the light source and the holding plate. When a part of energy of the light propagated through the inside of the object is absorbed by a light absorber (which resultantly becomes a sound source) such as blood, an acoustic wave (typically, an ultrasound wave) is generated by thermal expansion of the light absorber. The acoustic wave generated in the object is received by the probe through the holding plate. There is a degree of freedom in a positional relation between the light source and the probe. For example, the light source and the probe may be present on the same side with respect to the object or may be arranged to hold the object therebetween.

(Light Source)

When the object is a living organism, the light source irradiates light having wavelength absorbed by a specific component among components included in the living organism. The light source may be provided integrally with the photoacoustic signal acquiring apparatus according to this embodiment or may be provided separately from the photoacoustic signal acquiring apparatus. In order to efficiently generate an acoustic wave, pulse width is suitable about 10 to 50 nanoseconds. A laser that can obtain a large output is desirable as the light source. A light-emitting diode, a flash lamp, or the like can also be used instead of the laser. As the laser, various lasers such as a solid-state laser, a gas laser, a dye laser, and a semiconductor laser can be used. Timing, a waveform, intensity, and the like of the irradiation of the light is controlled by a not-shown light-source control unit. The light-source control unit may be integrated with the light source. The wavelength of the light source used in the present invention is desirably wavelength that allows the light to propagate to the inside of the object. Specifically, when the object is a living organism, the wavelength is equal to or larger than 600 nm and equal to or smaller than 1100 nm.

(Object and Light Absorber)

The object and the light absorber do not configure a part of the photoacoustic signal acquiring apparatus. However, the object and the light absorber are explained below. The photoacoustic signal acquiring apparatus that makes use of the photoacoustic effect according to the present invention is used mainly for imaging of a blood vessel, diagnosis of malignant tumors, vascular diseases, and the like of a human and an animal, follow-up of a chemical treatment, and the like. Therefore, as the object, a living organism, specifically, a target region of diagnosis such as a breast, a finger, or a limb of a human body or an animal is assumed. The light absorber on the inside of the object relatively has a high absorption coefficient in the object depending on the wavelength of light in use. Specific examples of the light absorber include water, fat, protein, oxygenated hemoglobin, and reduced hemoglobin.

(Probe)

The probe receives an acoustic wave generated on a living organism surface, inside of the living organism, and the like by pulsed light. The probe converts the acoustic wave into an electric signal, which is an analog signal. Any probe may be used as the probe as long as the probe that can receive an acoustic wave signal such as a probe that makes use of a piezoelectric phenomenon, a probe that makes use of resonance of light, or a probe that makes use of a change in capacitance. The probe in this embodiment is desirably a probe in which, typically, a plurality of receiving elements are one-dimensionally or two-dimensionally arranged. By using such multi-dimensionally arrayed elements, it is possible to simultaneously receive an acoustic wave in a plurality of places and reduce a measurement time. When the probe is smaller than a measurement target, the probe may be scanned to receive the acoustic wave in a plurality of positions. The acoustic wave received by the probe is converted into an electric signal and then, after being objected to amplification, digital conversion, or the like according to necessity, used for generation of property information in a processing unit.

(Holding Plate)

A material having acoustic impedance close to the acoustic impedance of the object is used as a holding plate in order to acoustically couple the probe and the object. In order to receive an acoustic wave efficiently, it is desirable to set the probe and the holding plate in contact with each other via liquid such as water, gel, or the like. When light is irradiated on the object through the holding plate, the holding plate needs to be transparent to the light from the light source. Examples of the holding plate include polymethylpentene. When the object is held by two holding plates and light is irradiated on the surface of the object on the opposite side of the probe, the acoustic impedance of one holding plate does not have to be taken into account. The one holding plate only has to be an optically transparent material in order to transmit light. Typically, a plastic plate of acrylic or the like, a glass plate, or the like is used. The holding plate is supported by the supporting unit explained below. The holding plate includes a first joining region. The holding plate is equivalent to a holding unit of the present invention.

(Supporting Unit)

The supporting unit is a section for suppressing deformation of the holding plate due to a load from the object. Typically, the supporting unit is configured by a plate-like member, an end of which is joined to an end of the holding plate. The supporting unit is fixed to the holding plate by screws, an adhesive, or the like. The supporting unit includes a second joining region. When the supporting unit is present within a view angle of the probe, a dead space in which photoacoustic signal measurement cannot be performed is formed. Therefore, it is desirable to reduce the thickness of the supporting unit as much as possible in order to reduce the dead space. Therefore, a material having a large Young's modulus is desirable. Examples of the material include tungsten carbide having a Young's modulus about two times as large as the Young's modulus of iron. In the case of an apparatus with which an examinee hangs down the breast in a prone position, the holding plate is considered to be supported by the supporting unit not to topple. At this point, the supporting unit supports the chest wall of the examinee. The supporting unit is considered to support the holding plate against stress caused when the breast is pressured to thereby prevent deformation of the holding plate. In the case of an apparatus with which the examinee places the breast on the holding plate in an upright position, the chest wall is supported by the supporting unit and the holding plate is supported by the supporting unit from below to keep the position and the shape of the holding plate.

(Light Reflecting Member)

The light reflecting member is used for suppressing light emitted to the outside of the object by light diffusion from being absorbed by the supporting unit for the holding plate. For example, a light reflecting film can be provided on a contact surface of the holding plate and the supporting unit. As the light reflecting film, a dielectric multilayer film or a metal film designed according to the wavelength of light to be irradiated can be used. As the light reflecting member, a member having reflectance higher than that of the member configuring the supporting unit is desirable. Specifically, the reflectance of the light reflecting film is desirably equal to or higher than 80% at wavelength in use. For example, when light in a range of wavelength equal to or longer than 600 nm and equal to or shorter than 1100 nm is used as irradiation light, a light reflection film including a gold film is suitably used as the light reflection film. When the gold film is used, it is also possible to attach a film of chrome or titanium between the gold film and the supporting unit in order to prevent the gold film from easily peeling from the supporting unit. The light reflecting member may be provided over the entire surface of the supporting unit or may be provided on a joining region of the holding plate to the supporting unit or a joining region of the supporting unit to the holding plate. It is also possible to insert the light reflecting member between the holding plate and the supporting unit. It is more effective to provide the light reflecting member around a joining region of the holding plate and the supporting unit as well.

First Embodiment

In a first embodiment, an example in which an object is held to be pressed against a holding plate is explained. FIG. 1 is a diagram for explaining this embodiment. Reference numeral 101 denotes a light source, 102 denotes a light transmission system, 103 denotes light, 104 denotes an illumination optical system, and 105 denotes a holding plate. Reference numeral 106 denotes an object, 107 denotes a light absorber, and 108 denotes an acoustic wave. Reference numeral 109 denotes a probe, 110 denotes an acoustic matching agent, 111 denotes a supporting unit, and 112 denotes a light reflecting member. In FIGS. 2A to 2C, reference numeral 113 denotes a first joining region in the holding plate 105 and 114 denotes a second joining region in the supporting unit 111.

In this embodiment, a wavelength-variable titanium-sapphire laser is used as the light source 101. The pulse width of the titanium-sapphire laser is 10 nanoseconds, the frequency thereof is 10 Hz, and the wavelength thereof is 797 nm. Light emitted from the light source 101 is transmitted by the light transmission system 102 including a bundle fiber. The transmitted light 103 is processed into a desired light distribution shape by the illumination optical system 104 including a lens and a mirror and irradiated on the object 106 through the holding plate 105. In order to efficiently receive the acoustic wave from the object, the holding plate 105 is desirably a holding plate having high transmittance to light having the wavelength of the light source and high transmittance to the acoustic wave. In this embodiment, a holding plate having thickness of 7 mm made of polymethylpentene is used.

The light 103 irradiated on the object 106 propagates while diffusing in the object 106. A part of the light 103 is absorbed by the light absorber 107 such as a blood vessel. The light absorber 107 that absorbs the light 103 generates the acoustic wave 108 according to the photoacoustic effect. The acoustic wave 108 propagates in the object 106. A part of the acoustic wave 108 is received by the probe 109. As the probe 109, a piezoelectric probe made of PZT (lead zirconate titanate) is used. In order to realize acoustic matching of the holding plate 105 and the probe 109, the acoustic matching agent 110 including castor oil is provided between the holding plate 105 and the probe 109. The holding plate 105 is supported by the supporting unit 111 made of tungsten carbide having thickness of 3 mm. As shown in the figure, a part of the irradiated light 103 diffuses and propagates in the direction of the supporting unit 111 as well passing through the object 106 and causes generation of an acoustic wave due to the photoacoustic effect.

A position where the light reflecting member 112, which is a characteristic of the present invention, is explained with reference to FIGS. 2A to 2C. FIG. 2A is a diagram for explaining a position where the light reflecting member 112 in this embodiment is provided. The holding plate 105 includes the first joining region 113 joined to the supporting unit 111. The supporting unit 111 includes the second joining region 114 joined to the holding plate 105. In this embodiment, a gold film is vapor-deposited on the second joining region 114 as the light reflecting member 112. The thickness of the gold film is 2000 angstroms. When the reflectance of the gold film was measured, the reflectance was 88% of the reflectance of light having wavelength of 797 nm made perpendicularly incident on the gold film. The reflectance of tungsten carbide not affixed with the gold film was 20% of the light having wavelength of 797 nm made perpendicularly incident on the tungsten carbide.

Figure 3:
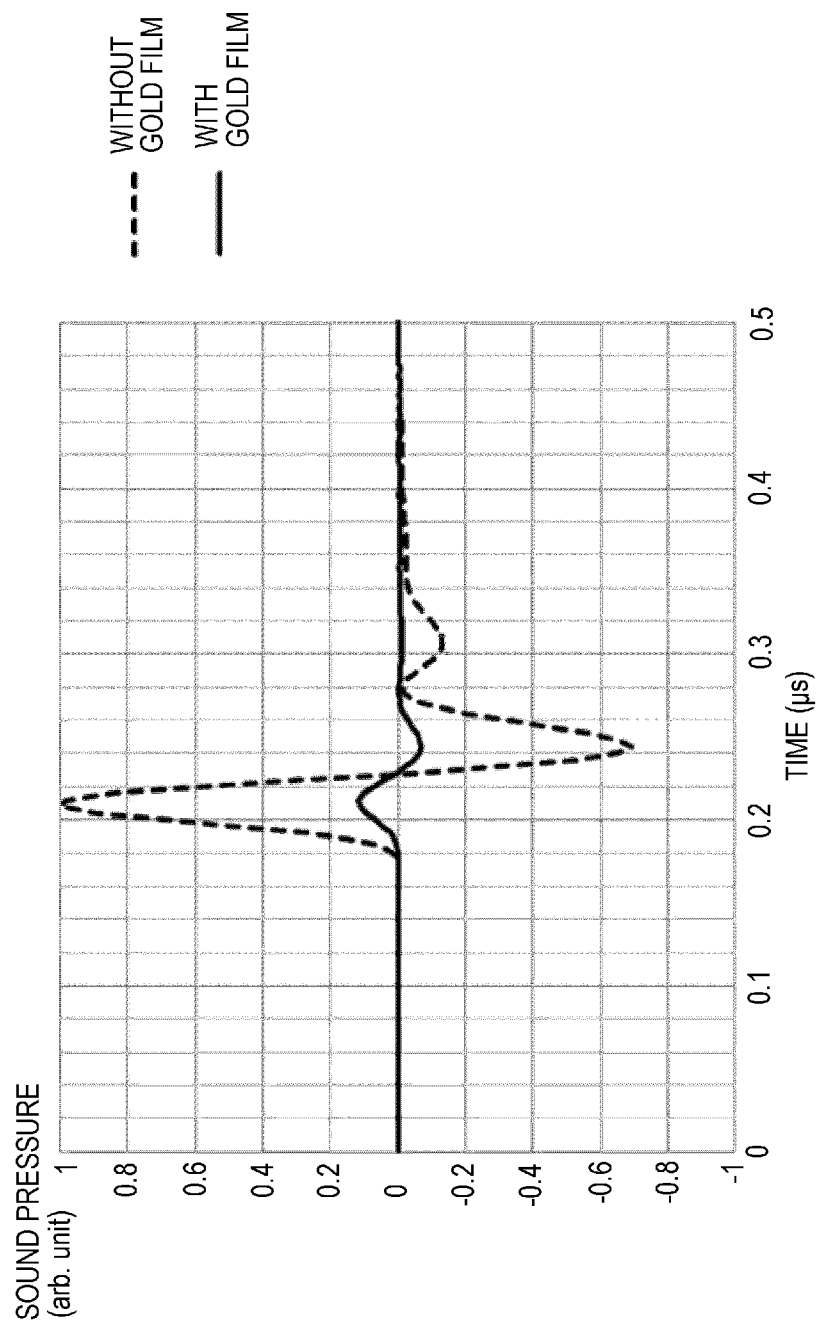
FIG. 3 is a graph showing sound pressure of an acoustic wave generated in a supporting unit.

Measured values of time waveforms of acoustic waveforms generated from the supporting unit when the gold film is not affixed to the supporting unit and when the gold film is affixed to the supporting unit are shown in FIG. 3. The ordinate represents sound pressure (intensity of an acoustic wave) and the abscissa represents elapsed time after light irradiation. The intensity of the acoustic wave is standardized by the intensity of an acoustic wave generated when the gold film is not affixed to the tungsten carbide. As it is seen from FIG. 3, by affixing the gold film to the tungsten carbide, compared with the intensity of the acoustic wave generated when the gold film is not affixed, the intensity of the acoustic wave generated from the tungsten carbide is reduced to 12%. This result indicates that noise deriving from the acoustic wave generated in the supporting unit is reduced and it is possible to accurately measure, with the probe, an acoustic wave signal generated in the object. In this way, it is possible to perform highly accurate photoacoustic signal measurement by providing the light reflecting member on the surface of the supporting unit.

In this embodiment, the light reflecting member 112 is provided on the second joining region 114. However, a place where the light reflecting member 112 is provided is not limited to this. Specifically, the light reflecting member 112 may be provided on the first joining region 113 as shown in FIG. 2B or may be inserted between the first joining region 113 and the second joining region 114 as shown in FIG. 2C. The place where the light reflecting member 112 is provided can be freely determined according to, for example, easiness to provide the light reflecting member. When the light reflecting member 112 is inserted between the first joining region 113 and the second joining region 114, for example, it is suitable to use a polycarbonate film affixed with the gold film. It is effective to provide the light reflecting member 112 around a joining region of the holding plate 105 and the supporting unit 111 as well because the generation of an acoustic wave due to light that scatters in the object 106 and reaches the joining region is further suppressed. Irrespective of where the light reflecting member 112 is provided, it is possible to fix the light reflecting member 112 by joining the end of the holding plate 105 and the supporting unit 111. It is also possible to guide the breast of an examinee, which is the object 106, to the holding plate 105.

In this embodiment, the holding plate 105 having a parallel flat plate shape is described. However, the holding plate 105 is not limited to this. A holding plate having, for example, a bowl shape or a cylindrical shape can also be used. Gold is described as the light reflecting member 112. However, the light reflecting member 112 is not limited to this. Aluminum or the like can also be used.

Second Embodiment

In a second embodiment, an example in which a light source and a probe are arranged on the same side with respect to a breast in a photoacoustic imaging apparatus for breast examination performed by holding the breast between two holding plates is explained. The apparatus configuration in this embodiment is effective for obtaining living organism information from a region close to the probe.

Figure 4A:
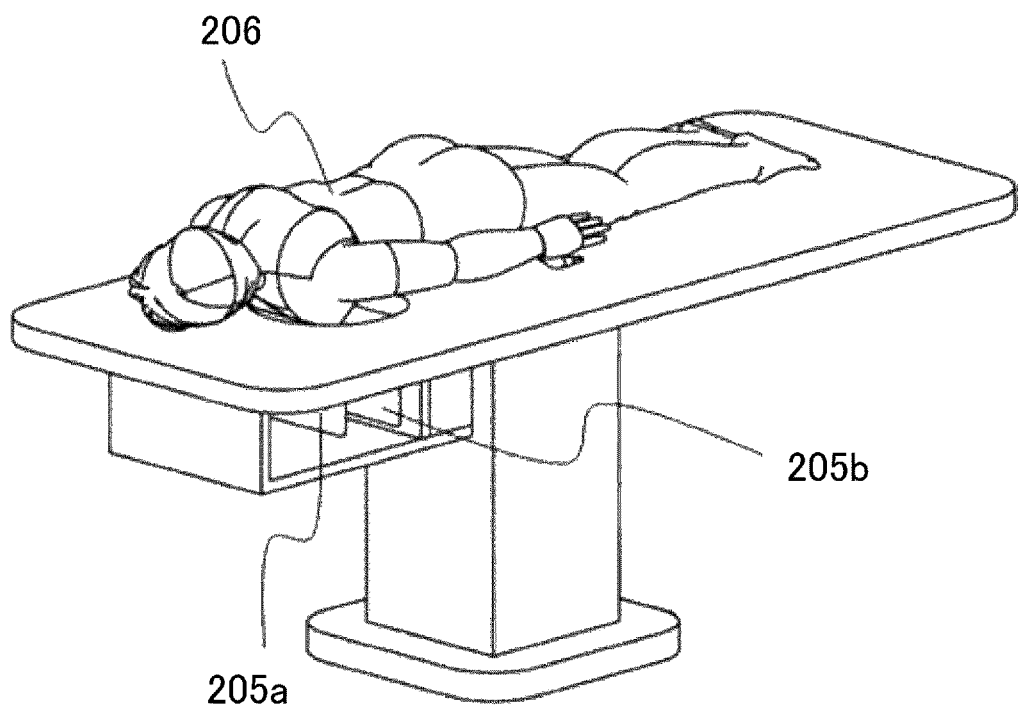
FIG. 4A is a perspective view showing the configuration of an apparatus according to a second embodiment.
Figure 4B:
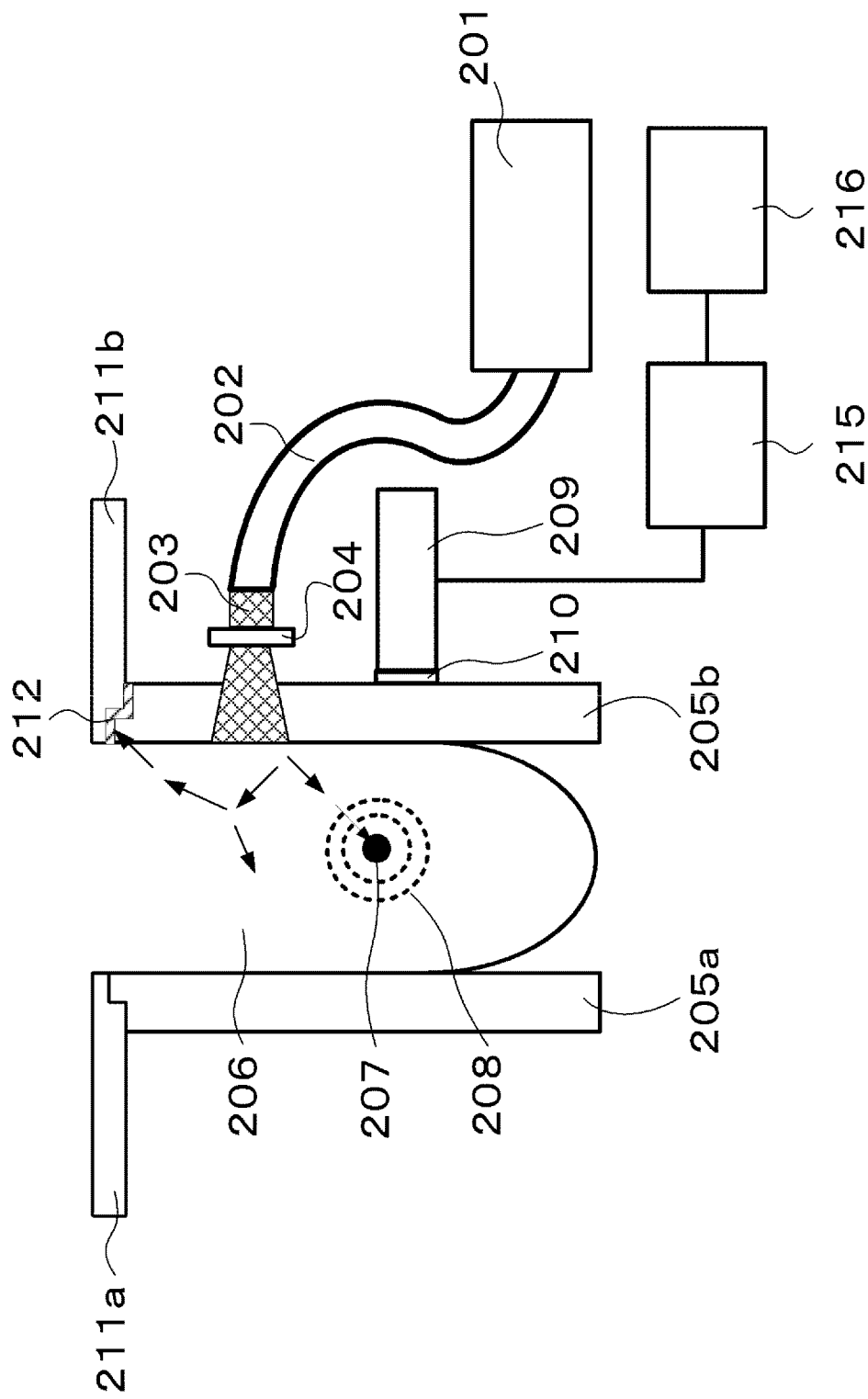
FIG. 4B is a schematic configuration diagram showing functional blocks of the apparatus according to the second embodiment.
Figure 4C:
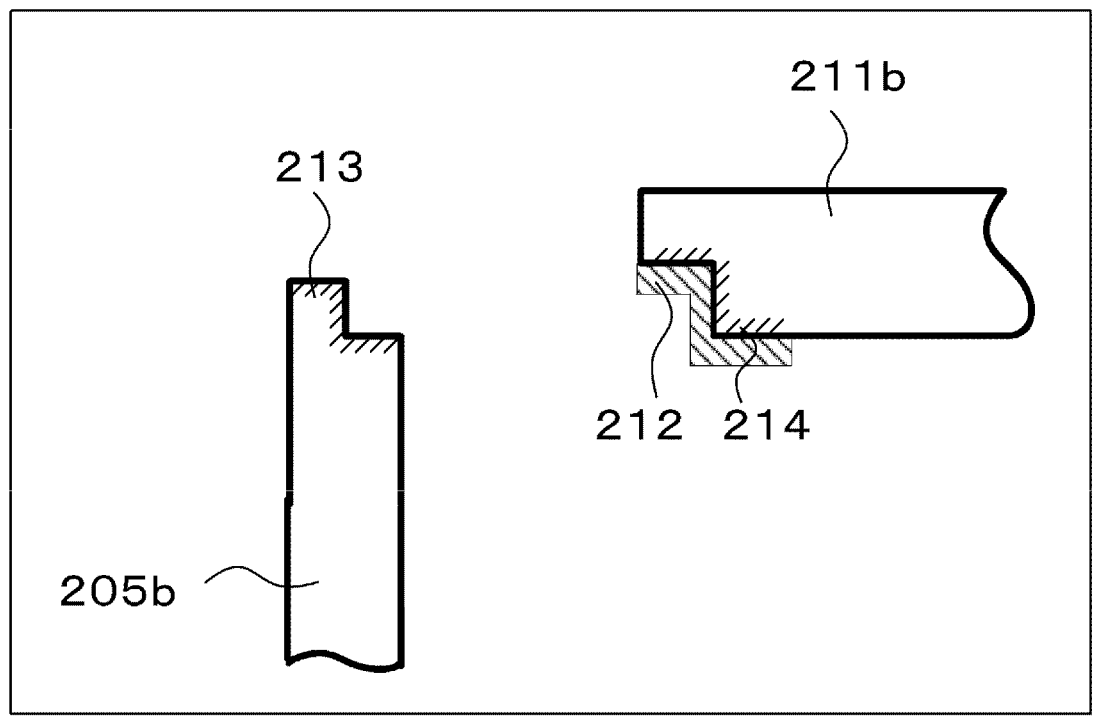
FIG. 4C is a diagram showing the arrangement of a light reflecting member in the second embodiment.

FIG. 4A is a schematic diagram of the photoacoustic imaging apparatus. FIG. 4B is an apparatus configuration diagram around a breast 206, which is the object. Reference numeral 201 denotes a light source, 202 denotes a light transmission system, 203 denotes light, 204 denotes an illumination optical system, 205a denotes a first holding plate, and 205b denotes a second holding plate. Reference numeral 206 denotes an object (an examinee), 207 denotes a light absorber, 208 denotes an acoustic wave, 209 denotes a probe, and 210 denotes an acoustic matching agent. Reference numeral 211a denotes a first supporting unit, 211b denotes a second supporting unit, 212 denotes a light reflecting member, 215 denotes a processing unit, and 216 denotes an image display unit. In FIG. 4C, reference numeral 213 denotes a first joining region in the second holding plate 205b and 214 denotes a second joining region in the second supporting unit 211b.

In this embodiment, a wavelength-variable titanium-sapphire laser is used as the light source 201. The pulse width of the titanium-sapphire laser is 10 nanoseconds, the frequency thereof is 10 Hz, and the wavelength thereof is 797 nm. Light emitted from the light source 201 is transmitted by the light transmission system 202 including a bundle fiber. The transmitted light 203 is processed into a desired light distribution shape by the illumination optical system 204 including a lens and a mirror and irradiated on the object 206 through the second holding plate 205b. In order to efficiently receive the acoustic wave from the object 206, the second holding plate 205b is desirably a holding plate having high transmittance to light having the wavelength of the light source 201 and high transmittance to the acoustic wave 208. In this embodiment, a holding plate having thickness of 7 mm made of polymethylpentene is used. The material and the thickness of the first holding plate 205a on the opposite side are not limited as long as the first holding plate 205a can hold the breast. In this embodiment, acrylic having thickness of 10 mm is used.

The light 203 irradiated on the object 206 propagates while diffusing in the object 206. A part of the light 203 is absorbed by the light absorber 207 such as a blood vessel. The light absorber 207 that absorbs the light 203 generates the acoustic wave 208 according to the photoacoustic effect. The acoustic wave 208 propagates in the object 206. A part of the acoustic wave 208 is received by the probe 209. As the probe 209, a piezoelectric probe made of PZT is used. In order to realize acoustic matching of the second holding plate 205b and the probe 209, the acoustic matching agent 210 including castor oil is provided between the second holding plate 205b and the probe 209. A signal received by the probe 209 is sent to the processing unit 215, converted into image information such as an initial sound pressure distribution and an absorption coefficient distribution of the inside of the object 206, and displayed on the image display unit 216. This processing corresponds to generation of property information. The first holding plate 205a and the second holding plate 205b are respectively supported by the first supporting unit 211a and the second supporting unit 211b. In order to bear a load due to pressuring and a load due to the weight of the object 206, a joining region between the first holding plate 205a and the first supporting unit 211a and a joining region between the second holding plate 205b and the second supporting unit 211b are machined in a step shape.

FIG. 4C is a diagram showing a position where the light reflecting member 212 is provided. The second holding plate 205b includes the first joining region 213 joined to the second supporting unit 211b. The second supporting unit 211b includes the second joining region 214 joined to the second holding plate 205b. A gold film is vapor-deposited on the second joining region 214 as the light reflecting member 212. The thickness of the gold film is 2000 angstroms. An acoustic wave generated in the second supporting unit 211b is directly received by the probe 209. Alternatively, the acoustic wave propagates while reflecting in the second holding plate 205b to be received by the probe 209. Therefore, the influence of noise of the acoustic wave is large. On the other hand, since the first supporting unit 211a is far from the light source 201 and the probe 209, the influence of noise due to an acoustic wave generated in the first supporting unit 211a is small. Therefore, in this embodiment, the light reflecting member 212 is provided only between the second holding plate 205b and the second supporting unit 211b. A light reflecting member is not provided between the first holding plate 205a and the first supporting unit 211a. However, a light reflecting member can also be provided between the first holding plate 205a and the first supporting unit 211a.

By adopting the configuration explained above, in the light 203 irradiated on the object 206, components emitted from the object 206 because of scattering and irradiated in the direction of the supporting units are reflected by the gold film. Then, an amount of light absorbed by the second supporting unit 211b decreases and the acoustic wave generated in the second supporting unit 211b decreases. As a result, noise deriving from the acoustic waves generated in the supporting units is reduced. It is possible to obtain a satisfactory photoacoustic image with little artifact.

Third Embodiment

In a third embodiment, an example in which a light source and a probe are arranged on the opposite sides across a breast in a photoacoustic imaging apparatus for breast examination performed by holding the breast between two holding plates is explained. The apparatus configuration in this embodiment is effective for obtaining living organism information from a region far from the probe.

Figure 5:
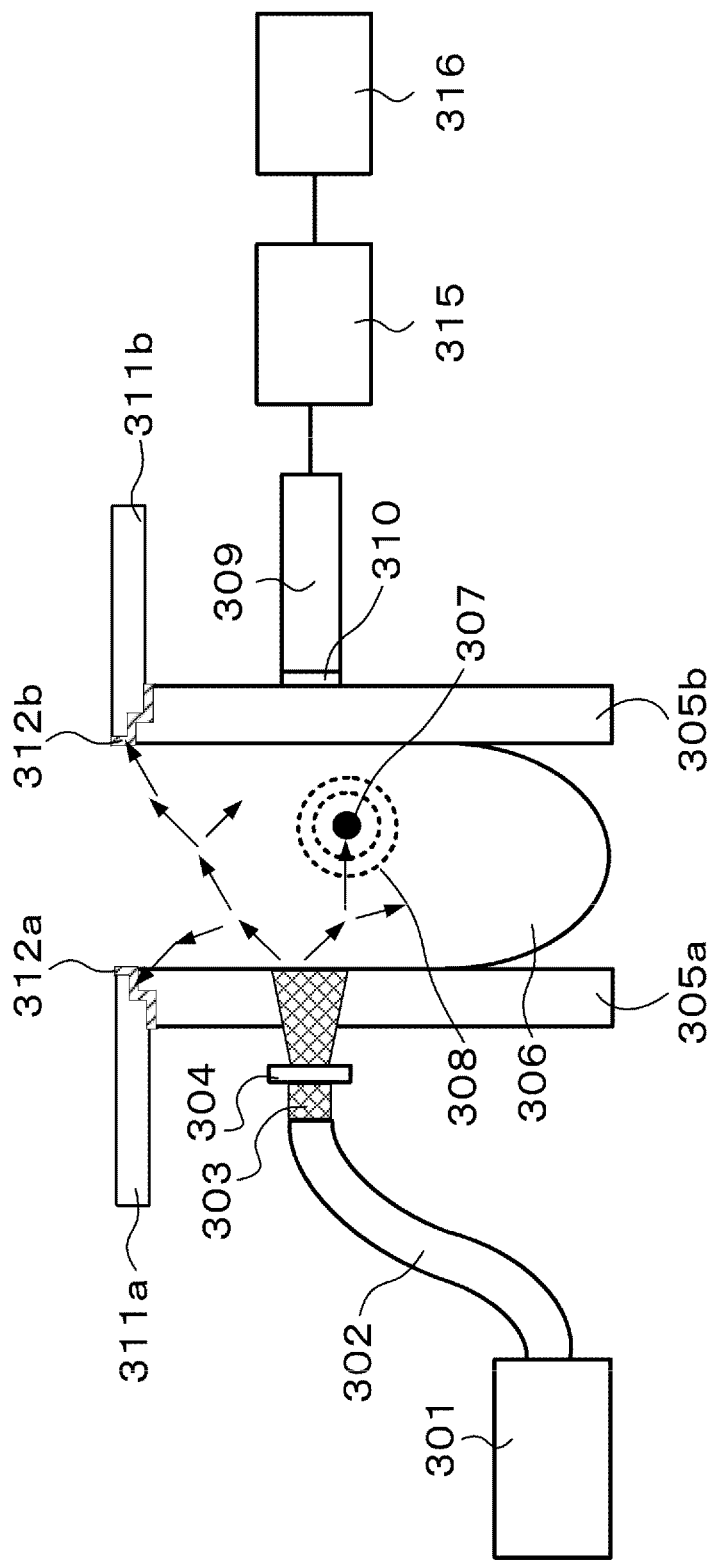
FIG. 5 is a schematic configuration diagram showing functional blocks of an apparatus according to a third embodiment.

FIG. 5 is a diagram for explaining the third embodiment of the present invention. Reference numeral 301 denotes a light source, 302 denotes a light transmission system, 303 denotes light, 304 denotes an illumination optical system, 305a denotes a first holding plate, and 305b denotes a second holding plate. Reference numeral 306 denotes an object, 307 denotes a light absorber, 308 denotes an acoustic wave, 309 denotes a probe, 310 denotes an acoustic matching agent, 311a denotes a first supporting unit, and 311b denotes a second supporting unit. Reference numeral 312a denotes a first reflecting member and 312b denotes a second light reflecting member. Reference numeral 315 denotes a processing unit and 316 denotes an image display unit.

Figure 6A:
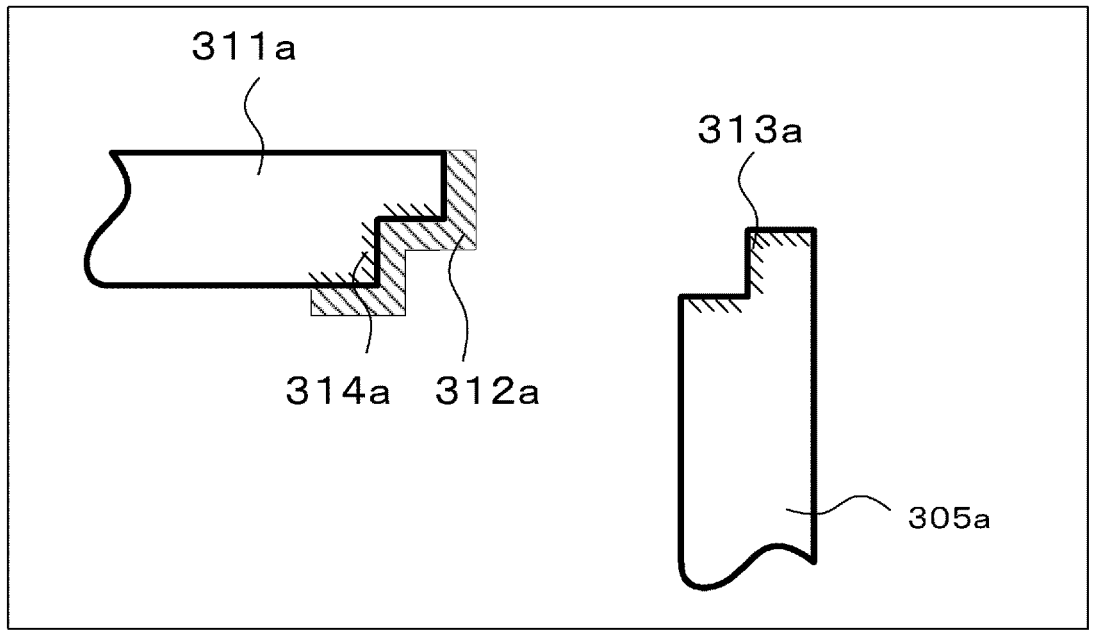
FIGS. 6A and 6B are diagrams showing the arrangement of a light reflecting member in the third embodiment.
Figure 6B:
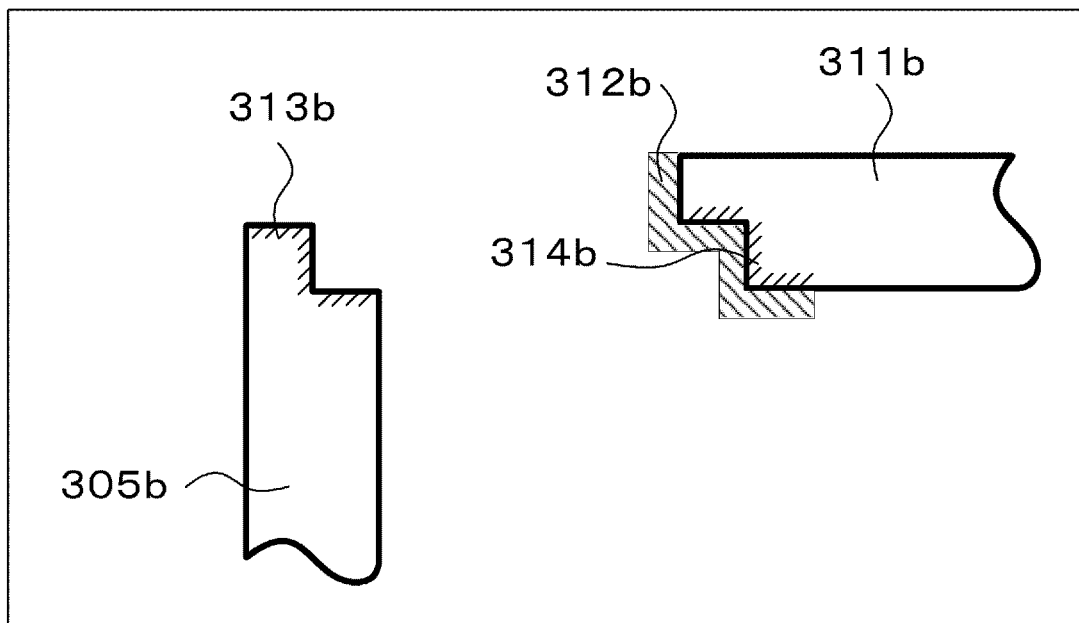

In FIGS. 6A and 6B, reference numeral 313a denotes a first joining region of the first holding plate 305a and reference numeral 314a denotes a second joining region of the first supporting unit 311a. Reference numeral 313b denotes a first joining region of the second holding plate 305b and 314b denotes a second joining region of the second supporting unit 311b.

In this embodiment, a wavelength-variable titanium-sapphire laser is used as the light source 301. The pulse width of the titanium-sapphire laser is 10 nanoseconds, the frequency thereof is 10 Hz, and the wavelength thereof is 797 nm. Light emitted from the light source 301 is transmitted by the light transmission system 302 including a bundle fiber. The transmitted light 303 is processed into a desired light distribution shape by the illumination optical system 304 including a lens and a mirror and irradiated on the object 306 through the first holding plate 305a. The first holding plate 305a on the light source 301 side is desirably a holding plate having high transmittance to light having the wavelength of the light source 301. In this embodiment, acrylic having thickness of 10 mm is used. On the other hand, in order to efficiently receive the acoustic wave 308 from the object 306, the second holding plate 305b on the probe 309 side is desirably a holding plate having high transmittance to the acoustic wave 308. In this embodiment, a holding plate having thickness of 7 mm made of polymethylpentene is used.

The light 303 irradiated on the object 306 propagates while diffusing in the object 306. A part of the light 303 is absorbed by the light absorber 307 such as a blood vessel. The light absorber 307 that absorbs the light 303 generates the acoustic wave 308 according to the photoacoustic effect. The acoustic wave 308 propagates in the object 306. A part of the acoustic wave 308 is received by the probe 309. As the probe 309, a piezoelectric probe made of PZT is used. In order to realize acoustic matching of the second holding plate 305b and the probe 309, the acoustic matching agent 310 including castor oil is provided between the second holding plate 305b and the probe 309. A signal received by the probe 309 is sent to the processing unit 315, converted into image information such as an initial sound pressure distribution and an absorption coefficient distribution of the inside of the object 306, and displayed on the image display unit 316.

The first holding plate 305a and the second holding plate 305b are respectively supported by the first supporting unit 311a and the second supporting unit 311b. In order to bear a load due to pressuring and a load due to the weight of the object 306, a joining region between the first holding plate 305a and the first supporting unit 311a and a joining region between the second holding plate 305b and the second supporting unit 311b are machined in a step shape. Since the first supporting unit 311a is close to the light source 301, the irradiation density of light emitted from the object 306 because of scattering and irradiated in the direction of the supporting units is high and a strong acoustic wave is generated. On the other hand, since the second supporting unit 311b is close to the probe 309, an acoustic wave generated in the second supporting unit 311b is received by the probe 309 before being sufficiently attenuated. Therefore, gold films are respectively provided as the first light reflecting member 312a and the second light reflecting member 312b between the first holding plate 305a and the first supporting unit 311a and between the second holding plate 305b and the second supporting unit 311b. Further, in order to suppress generation of an acoustic wave due to light directly irradiated on the supporting units not via the holding plates, a gold film is also provided on a region where the first supporting unit 311a and the second supporting unit 311b are in contact with the object 306 when the object 306 is held by the holding plates.

FIGS. 6A and 6B are diagrams showing, more in detail, positions where the gold films are provided. The first holding plate 305a includes the first joining region 313a joined to the first supporting unit 311a. The first supporting unit 311a includes the second joining region 314a joined to the first holding plate 305a. The second holding plate 305b includes the first joining region 313b joined to the second supporting unit 311b. The second supporting unit 311b includes the second joining region 314b joined to the second holding plate 305b. Both of the first light reflecting member 312a and the second light reflecting member 312b are gold films and are respectively vapor-deposited on the second joining regions 314a and 314b. The thickness of both the gold films is 2000 angstroms. As in the embodiments explained above, the positions where the light reflecting members are provided may be on the side of the first joining regions or may be between the supporting units and the holding plates.

By adopting the configuration explained above, in the light 303 irradiated on the object 306, components emitted from the object 306 because of scattering and irradiated in the direction of the supporting units are reflected by the gold films. In this embodiment, reflectance to light directly irradiated on the supporting units from the object not via the holding plates is also improved. Therefore, an amount of light absorbed by the supporting units is smaller than the amount of the light in the second embodiment. Then, acoustic waves generated in the first supporting unit 311a and the second supporting unit 311b decrease. As a result, noise deriving from the acoustic waves generated in the supporting units is reduced. It is possible to obtain a satisfactory photoacoustic image with little artifact.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-047005, filed on Mar. 2, 2012, which is hereby incorporated by reference herein its entirety.

What is claimed is:

1. An object information acquiring apparatus comprising:
   a light source;
   a holding plate configured to hold an object, said holding plate being transparent to light from said light source;
   a supporting unit configured to support said holding plate;
   a probe configured to receive, via said holding plate, an acoustic wave generated from the object on which light is irradiated from said light source; and
   a light reflecting member provided between said supporting unit and said holding plate, wherein said light reflecting member is in contact with both said supporting unit and said holding plate.

2. The object information acquiring apparatus according to claim 1, wherein said light reflecting member is provided on said holding plate.

3. The object information acquiring apparatus according to claim 1, wherein said light reflecting member is provided on said supporting unit.

4. The object information acquiring apparatus according to claim 1, wherein said light reflecting member is a member having reflectance higher than that of said supporting unit.

5. The object information acquiring apparatus according to claim 1, further comprising a processing unit configured to generate property information of an inside of the object on the basis of the acoustic wave.

6. An object information acquiring apparatus according to claim 1, wherein said supporting unit is further configured to support said holding plate via a joining region.

7. An object information acquiring apparatus according to claim 1, further comprising an optical member disposed between said light source and said holding plate, said optical member being at least one of a lens, a mirror, a diffuser, and an optical fiber.

8. An object information acquiring apparatus according to claim 1, wherein said holding plate includes polymethylpentene.

9. An object information acquiring apparatus according to claim 1, wherein said holding plate includes at least one of plastic and glass.

10. An object information acquiring apparatus according to claim 1, wherein said supporting unit is made from tungsten carbide.

11. An object information acquiring apparatus according to claim 1, wherein said light reflecting member includes at least one of a dielectric multilayer film and a metal film.

12. An object information acquiring apparatus according to claim 1, wherein said light reflecting member has a reflectivity of 80% or more at the wavelength of the light emitted from said light source.

13. An object information acquiring apparatus comprising:
   a light source;
   a holding plate configured to hold an object;
   a supporting unit configured to support said holding plate;
   a probe configured to receive, via said holding plate, an acoustic wave generated from the object; and
   a light reflecting member provided between said supporting unit and said holding plate,
   wherein said light reflecting member is in contact with both said supporting unit and said holding plate, and
   wherein said probe is configured to be moved to receive the acoustic wave in a plurality of positions.

* * * * *